United States Patent [19]

Johnson et al.

[11] Patent Number: 5,045,480

[45] Date of Patent: * Sep. 3, 1991

[54] GEL PARTICLES HAVING HAPTEN MOIETIES BOUND THERETO AS IMMUNOASSAY REAGENT

[75] Inventors: Richard D. Johnson, Elkhart, Ind.; H.-Volker Runzheimer, Bergisch Gladbach, Fed. Rep. of Germany; Ronald G. Sommer; Kin F. Yip, both of Elkhart, Ind.

[73] Assignee: Miles Inc., Elkhart, Ind.

[*] Notice: The portion of the term of this patent subsequent to Apr. 18, 2006 has been disclaimed.

[21] Appl. No.: 308,658

[22] Filed: Feb. 9, 1989

[51] Int. Cl.$^5$ .......................................... G01N 33/547
[52] U.S. Cl. .................................... 436/532; 436/531; 436/535
[58] Field of Search .............. 435/4, 7; 436/519, 520, 436/824, 532

[56] References Cited

U.S. PATENT DOCUMENTS

| | | |
|---|---|---|
| 3,793,445 | 2/1974 | Upkike et al. |
| 3,966,897 | 6/1976 | Renn et al. |
| 3,970,429 | 7/1976 | Updike |
| 4,200,436 | 4/1980 | Mochida et al. |
| 4,446,232 | 5/1984 | Liotta |
| 4,551,426 | 11/1985 | Freytag |
| 4,822,747 | 4/1989 | Johnson et al. ................... 436/532 |

OTHER PUBLICATIONS

Methods in Enzymology, vol. 34B(1974) pp. 30 et seq (Inman).
Biochemistry, vol. 8(1969) pp. 4074 et seq (Inman II).
Immunochemistry, vol. 9(1972) pp. 1077 et seq (Ohno).
Biochemistry, vol. 7(1975) pp. 1535 et seq (Schnaar).
Biopolymers, vol. 22(1983) pp. 839 et seq (Varadarajan).
JACS, vol. 101(1979) pp. 5383 et seq (Stahl).
An Introduction to Affinity Chromatography, ed. Lowe (North Holland) pp. 305-310 and 366-369.

*Primary Examiner*—Robert A. Wax
*Assistant Examiner*—David R. Preston
*Attorney, Agent, or Firm*—Daniel W. Collins; Andrew L. Klawitter

[57] ABSTRACT

An immobilized hapten reagent for use in a specific binding assay for the determination of a hapten or binding analog thereof in a liquid test sample and methods for preparing and using the immobilized hapten reagent. The immobilized hapten reagent comprises a hapten moiety covalently linked substantially only to the external surface of a gel particle. The immobilized hapten reagent is prepared by forming a reaction mixture comprising the hapten moiety and the carrier material in a nonswelling solvent wherein the gel particle is substantially impervious to the hapten moiety and wherein an analytically insignificant amount of the hapten moiety is nonspecifically bound to the gel particle. The immobilized hapten reagent is characterized by being substantially stable in aqueous solutions and exhibits an insignificant amount of leakage of the hapten moiety into a liquid test medium.

33 Claims, 2 Drawing Sheets

DOSE RESPONSE TO DIGOXIN

GEL PARTICLES HAVING HAPTEN MOIETIES BOUND THERETO AS IMMUNOASSAY REAGENT

BACKGROUND OF THE INVENTION

The present invention relates to specific binding assays and reagents for use therein for the determination of an analyte in a liquid test medium. In particular, the present invention relates to heterogeneous immunoassays for determining haptens employing immobilized hapten reagents for the separation of bound and free forms of a labeled reagent.

Various heterogeneous specific binding assays have been developed which generally involve specific binding interactions between the analyte to be detected, a specific binding partner for the analyte, and a labeled reagent, which can be the same or different as the binding partner for the analyte. When performing such assays, the labeled reagent becomes bound to its corresponding binding partner to generate a bound species, any of the labeled reagent not so bound being the free species, wherein the extent of binding is a function of the amount of analyte present. Where the detectable response of the labeled reagent is essentially indistinguishable in the bound species and the free species, it is necessary to physically separate such bound and free species from each other in order to effectively determine the amount of analyte present. Accordingly, once the bound and free species of the labeled reagent have been separated from each other, the amount of label present in either fraction thereof is determined by measuring the activity of the particular label of the labeled reagent and correlating such activity with the amount of analyte present.

The physical separation of the bound species from the free species can be accomplished in many ways. In the heterogeneous specific binding assay known as the immunometric assay, the labeled reagent comprises a labeled form of an anti-analyte antibody. According to such format, separation of the free labeled reagent from the bound labeled reagent is accomplished by addition of an immobilized form of the analyte under determination or an analog thereof which will bind with the antibody of the free labeled reagent. For example, U.S. Pat. No. 4,200,436 discloses an immunoassay for the detection of antigen employing an immobilized form of the antigen to be measured to separate the bound and free forms of a labeled monovalent antibody to the antigen. The immobilized form of the antigen is prepared by chemically binding or physically adsorbing the antigen to solid supports or carrier materials, such as polysaccharides or plastics, according to methods known in the art.

Similarly, U.S. Pat. No. 4,551,426 discloses a heterogeneous immunoassay for the hapten digoxin employing an immobilized form of ouabain (a digoxin analog) to separate the bound and free forms of an anti-digoxin labeled antibody. The immobilized form of ouabain is prepared by coupling ouabain, either directly or through a spacer arm such as a protein, polyamino acid, or synthetic linker, to a support material, such as beaded agarose, beaded dextran, polyacrylamide, or glass, according to methods known in the art.

Such support materials, however, together with the processes employed to couple the desired analyte or analog thereof (ligand) to such support materials, result in relatively unstable reagents, reagents exhibiting substantial release or leakage of the ligand into the surrounding liquid when used in an immunoassay as heretofore described. Such instability is believed to be the result of an instability in the linkage between the ligand and the support as well as nonspecific binding of the ligand to the support material. Such instability of the linkage and nonspecific binding of ligand results in a substantial amount of the ligand being slowly released or leaching into the surrounding medium. The leaching of the ligand into the test medium primarily occurs as a result of the ligand being nonspecifically bound to internal and external portions of the support material. Although inconvenient, ligand nonspecifically bound to the external surface can be removed by washing the support material with an aqueous wash solution prior to use in an assay procedure. However, ligand nonspecifically bound to internal portions cannot be effectively removed and such internalized ligand leaches out from the interior of the support material and into the liquid test medium where it can be substantially indistinguishable from analyte from a test sample and free to bind to the labeled reagent, resulting in an inaccurate measurement of the amount of analyte actually present in the test sample.

The synthesis and use of support materials, particularly crosslinked polymer supports, having chemical structures which are physiochemically compatible with the backbone structure of a peptide have also been described for use in solid-phase peptide synthesis. In particular, techniques for coupling peptides to a polymer [Stahl, et al., *J. Amer. Chem. Soc.*, Vol. 22, p. 839 (1983)] using reverse-phase suspension polymerization in aqueous organic solvent mixtures have been employed to obtain favorable swelling properties of such support materials in order to provide increased external and internal reaction sites.

Accordingly, it is an object of the present invention to provide an immobilized hapten reagent which is stable in aqueous solutions and which does not slowly release or leach hapten into a surrounding aqueous solution.

Further, it is an object of the present invention to provide a process of covalently binding a hapten moiety substantially only to the surface of a carrier material with substantially no internalization of nonspecifically bound hapten which would otherwise be slowly released or leached into the surrounding medium.

Another object of the present invention is to provide a stable, immobilized hapten reagent for use in an immunoassay for the effective immobilization and separation of the free species of a labeled reagent from its bound species.

It is still a further object of the present invention to provide a highly sensitive liquid immunoassay having a low, analytically insignificant initial background signal for the accurate determination of a hapten or binding analog thereof in a liquid test sample.

SUMMARY OF THE INVENTION

The present invention provides an immobilized hapten reagent which is substantially stable in an aqueous environment for use in a specific binding assay, particularly an immunoassay, for the determination of a hapten or binding analog thereof from a liquid test sample. The immobilized hapten reagent comprises a carrier material composed of a gel particle, and a plurality of hapten moieties bound thereto. The gel particle comprises a plurality of external and internal functional groups on the internal and external surfaces of the gel particle, respectively, wherein substantially all of the bound hapten moieties are covalently linked to the external surface functional groups by a linking group which is substantially stable in aqueous solutions, particularly immunoassay test mediums, and an analytically insignificant amount of the hapten moiety remains nonspecifically bound to the carrier material. Accordingly, substantially all of the hapten moiety remains covalently bound to the carrier material during the performance of an immunoassay and only an insignificant amount, if any, of the hapten moiety dissociates or leaches from the carrier material into the test medium.

According to the present invention, there is also provided a method of preparing the stable immobilized hapten reagent which minimizes the nonspecific binding of the hapten moiety to the gel particle, particularly the nonspecific binding of the hapten moiety to internal surface areas of the gel particle. The method comprises the steps of (a) reacting the hapten moiety with a gel particle comprising a plurality of external and internal chemically active functional groups in a solvent in which the gel particle is substantially nonswollen and under conditions to form a covalent bond between the hapten moiety and the external functional groups which is substantially stable in aqueous solutions, (b) washing the gel particle resulting from step (a) with a nonswelling solvent, (c) washing the gel particle resulting from step (b) with an aqueous buffer solution, and (d) isolating the immobilized hapten reagent resulting from step (c) comprising the gel particle and the hapten moieties bound thereto wherein substantially all of the bound hapten moieties are covalently linked to the external surface functional groups.

The gel particle is substantially nonswellable when reacted with the hapten moiety in the presence of the nonswelling solvent and, accordingly, is substantially impervious to the hapten moiety and the covalent binding thereof is limited substantially only to the external surface functional groups of the gel particle. Any of the hapten moiety which becomes nonspecifically bound to the external surface of the gel particle in step (a) is removed with the nonswelling and aqueous wash solutions of steps (b) and (c), respectively.

The immobilized hapten reagent is particularly useful in a heterogeneous specific binding assay involving binding between a hapten or binding analog thereof and a labeled reagent comprising a labeled binding partner for the hapten or binding analog thereof, wherein it is necessary to physically separate and of the labeled reagent which becomes bound to the hapten or binding analog thereof from the labeled reagent not so bound. Any of the labeled reagent which does not bind to the hapten or binding analog thereof from the test medium is separated from the bound labeled reagent by binding to the hapten of the immobilized hapten reagent wherein the extent of binding is a function of the amount of hapten or binding analog present in a liquid sample.

DESCRIPTION OF THE PREFERRED EMBODIMENTS

Figure 1:
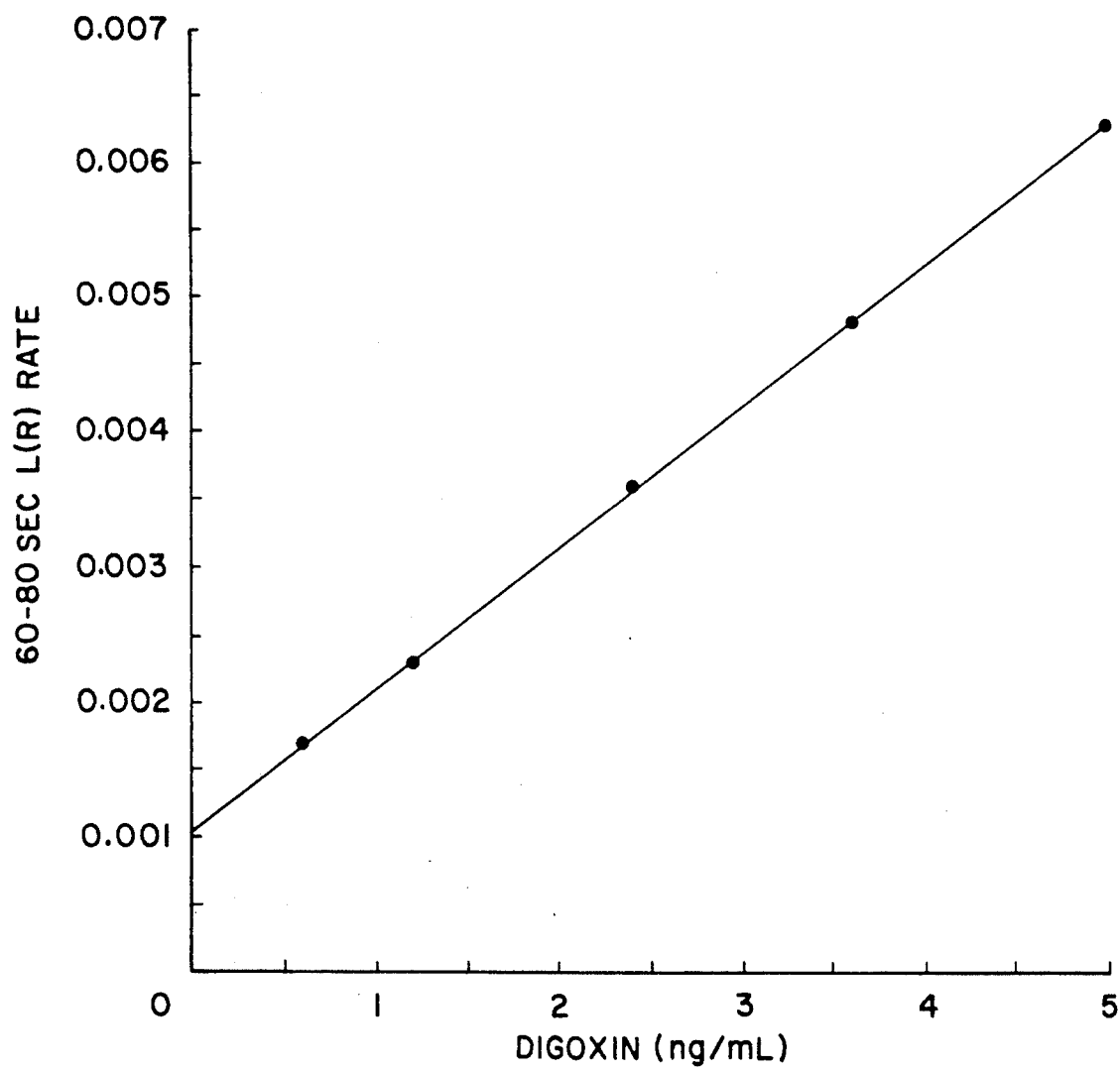
FIG. 1 is a graph which illustrates the dose response to digoxin generated in an immunoassay employing digitoxigenic as the hapten moiety in an immobilized hapten reagent of the present invention.

The immobilized hapten reagent of the present invention can be employed in conventional heterogeneous specific binding assay methods, particularly heterogeneous enzyme immunoassays, involving binding between a hapten or binding analog thereof and a labeled reagent comprising a labeled form of a specific binding partner for the hapten or binding analog thereof. Furthermore, the hapten component of the immobilized hapten reagent can be varied for use in such specific binding assay for the detection of any hapten or binding analog thereof for which a specific binding partner exists in biological systems or can be synthesized. Where the specific binding partner for the hapten or binding analog thereof is an anti-hapten, such as an antibody to the hapten or fragment thereof, such specific binding assay method is referred to as an immunometric method.

According to such heterogeneous specific binding assay methods, particularly the immunometric method, the hapten or binding analog thereof being detected is generally combined with the labeled reagent to form a reaction mixture wherein the labeled reagent binds to the hapten being detected. The extent of such binding is then determined and related to the hapten to be determined. The ratio of the amount of labeled reagent bound to the hapten being detected (i.e., the bound species) to the amount of labeled reagent not so bound (i.e., the free species) is a function of the amount of hapten present. Since the signals generated by the label of the labeled reagent of both the bound and free species thereof are indistinguishable, it is necessary to physically separate the free species from the bound species to permit the independent determination of the amount of label present in the one or the other, which determination can then be correlated to the amount of hapten present.

The immobilized hapten reagent of the present invention is particularly useful for the separation of the free species of a labeled anti-hapten antibody from the bound species of such anti-hapten antibody in a specific binding assay wherein the free species binds to and is immobilized by the immobilized hapten reagent to achieve the necessary separation step. In particular, the immobilized hapten reagent of the present invention comprises an appropriately functionalized gel particle carrier material and a plurality of hapten moieties bound thereto. The gel particle comprises a plurality of external and internal functional groups and substantially all of the bound hapten moieties are covalently linked substantially only to the external surface groups of the gel particle by a linking group. The linking group provides a covalent bond which is substantially stable in aqueous solutions, particularly in aqueous solutions comprising the liquid test medium of an immunoassay, wherein the hapten moiety remains covalently bound to the carrier material during the performance of an immunoassay to effectively separate the free species from the bound species. It is to be appreciated that such stability in aqueous environments prevents the dissociation of the hapten moiety from the carrier material and, accordingly, leaching of the hapten moiety into the test medium environment to thereby result in decreased assay sensitivity and accuracy, as will be described in greater detail hereinafter.

According to a preferred embodiment of the present invention, the immobilized hapten reagent is particularly useful in an immunoassay for the detection of digoxin from a liquid test sample. The labeled reagent comprises an enzyme-labeled monovalent antibody fragment derived from a monoclonal antibody against digoxin, preferably the Fab' fragment of a monoclonal IgG antibody to digoxin, generally obtained according to methods known in the art and labeled with an enzyme, preferably $\beta$-D-galactosidase. Preferably, the labeled reagent is electrophoretically purified on an electrophoretic polyacrylamide gel to result in a substantially pure monoconjugate preparation thereof comprising a single monovalent antibody fragment component covalently linked to a single enzyme component according to the method described in European Patent Application Publication No. 270,930.

The immunoassay for digoxin is performed by reacting the labeled reagent, preferably the monoconjugate preparation thereof, with a test sample containing digoxin, and then adding the immobilized hapten reagent of the present invention comprising digoxin or an analog thereof, such as digitoxigenin, covalently linked to the external surface amine groups of an amine functionalized polyacrylamide carrier material by a linking group, as will be described in greater detail hereinafter. Where the hapten moiety of such immobilized hapten reagent comprises digoxin or an analog of digoxin, such as digitoxigenin, the digoxin from the liquid test sample binds to the antibody fragment of the labeled reagent to form the bound species thereof, and any of the free species of the labeled reagent which does not bind to digoxin from the test sample binds to the immobilized hapten reagent for the immobilization and subsequent separation thereof from the bound species, wherein the bound species remains in solution and the free species settles out from solution. The amount of digoxin in the test sample is then determined by measuring the enzyme activity of the bound species of the labeled reagent.

According to another preferred embodiment of the present invention, the immobilized hapten reagent comprises a glycosylated peptide sequence, such as corresponding to the glycosylated N-terminal peptide sequence in the beta-subunit of human hemoglobin (glycopeptide), covalently linked to the external surface sulfhydryl groups of a polyacrylamide-sulfhydryl derivatized carrier material, such as described in European Patent Application Publication No. 270,949, which is useful in an immunoassay for the determination of HbAlc. The labeled reagent comprises a monovalent antibody fragment derived from a monoclonal antibody specific for the glucosylated N-terminal peptide sequence in the beta-subunit of human hemoglobin (see European Patent Application Publication No. 185,870) labeled with $\beta$-D-galactosidase and purified to a monoconjugate preparation thereof as heretofore described, and the amount of HbAlc in the liquid test sample is determined by measuring the enzyme activity of the bound species of the labeled reagent.

The measurement of the enzyme activity in such immunoassays is accomplished by removing an aliquot of supernatant and depositing the aliquot onto a reagent pad incorporated with a chromogenic substrate for the enzyme label, such as resorufin-$\beta$-D-galactopyranoside, o-nitrophenol-$\beta$-D-galactopyranoside, or, more preferably, a chromogenic acridinone enzyme substrate for $\beta$-D-galactosidase comprising a 7-hydroxy-9H-acridin-2-one chromogen derivatized with a $\beta$-D-galactose residue such as described in European Patent Application Publication No. 270,946. The detectable signal which is generated by the interaction between the enzyme and the chromogenic substrate is then measured with, for example, a reflectance photometer, and correlated to the amount of hapten present in the liquid test sample.

IMMOBILIZED HAPTEN REAGENT

It is to be appreciated that in order to provide a highly sensitive immunoassay to accurately determine the amount of hapten present in a liquid test sample, nonspecific binding of the hapten moiety to the carrier material should be minimized. Any of such nonspecifically bound hapten moiety otherwise results in the dissociation of the hapten moiety from the carrier material and the slow release or leaching thereof into the liquid immunoassay test medium as a free hapten species which competes with the hapten from the test sample for binding to the labeled reagent. Accordingly, the label of the labeled reagent bound to such dissociated hapten moiety provides a background signal which will interfere with the detection of the signal provided by the label of the labeled reagent bound to the hapten from the test sample to result in an inaccurate determination of the hapten being detected from the liquid test sample.

Accordingly, an important feature of the present invention is to provide an immobilized hapten reagent which is substantially stable in aqueous solutions and which comprises a hapten moiety covalently linked substantially only to the external surface of an appropriately functionalized gel particle carrier material, with only an analytically insignificant amount, if any, of the hapten moiety nonspecifically bound thereto.

According to the present invention, control of nonspecifically bound hapten to within acceptable limits is achieved by reacting the hapten moiety with a carrier material comprising an appropriately functionalized or derivatized resin in a nonswelling solvent in the presence of a link in group which forms a substantially stable, covalent bond therebetween to provide an immobilized hapten reagent which is substantially stable in aqueous solutions. The nonswelling solvent limits the extent of covalent binding substantially only to the external surface functional groups of the carrier material, as will be described in greater detail hereinafter.

(a) Carrier Material

The carrier material of the immobilized hapten reagent can be selected from various water swellable gel particles which are known in the art or which can be prepared according to methods known in the art. The carrier material is functionalized or capable of being functionalized with appropriate chemically active functional groups for covalently binding to the hapten moiety according to the present invention. Further, the carrier material is a gel particle which, while swellable in aqueous media, is substantially nonswellable in one or more solvents which are compatible with the coupling reaction by which the hapten moiety is linked to the gel particle. As will be described in greater detail below, an appropriate solvent or solvents for a particular gel particle can be selected from various nonswelling solvents known in the art, preferably organic solvents containing little or no water, and include, without limitation, dimethylsulfoxide, dimethylformamide, acetone, chlorinated hydrocarbons, cyclic and acyclic alkylethers, and the like.

The gel particle can be made of polymeric materials, such as, without limitation, polymers and/or copolymers of acrylic acid, agarose, cellulose, dextran, their derivatives or mixtures thereof, and the like. In particular, such particles can be made from polymeric materials such as polystyrene, polyacrylatex, polyacrylamide, or naturally occurring materials such as polysaccharides, particularly crosslinked polysaccharides, such as agarose (e.g., Sepharose®), dextran (e.g., Sephadex®), microcrystalline cellulose, starch, cellulose fibers, and the like. Other materials include polyvinyltoluene, or styrenebutadiamine copolymers, polyacrolein microspheres, polyurethane, pollen particles, sporopollenin, polystyrene or polyvinylnaphthalene cores surrounded by shells of polyclycidyl methacrylate, microcrystalline cellulose or combinations thereof, polyvinyl alcohol, copolymers of hydroxyethyl methacrylate and methyl methacrylate, and the like.

Although the gel particle is generally in the form of a bead, other configurations may be employed as well, such as, without limitation, rods, fibers, geometric configurations, and the like, and irregular configurations thereof. The dimensions of the gel particle can vary and essentially any size gel particle can be employed. Generally, the dimensions of such gel particles are from less than about 1,000 microns, preferably from between about 0.001 microns and about 850 microns, more preferably from between about 37 microns and about 75 microns.

Generally, the physical structure of such gel particles comprises crosslinked chains of the respective polymers and/or copolymers which define an external surface area and an internal surface area wherein the accessibility of the hapten moiety and other reagents to the internal surface area is limited when the gel particle is non-swollen as heretofore described. It is to be understood that the swelling characteristic of the gel particle is the result of the structural network cf the cross-linked chains which result in a generally porous nature of the gel particle. Accordingly, when the gel particle is non-swollen, the polymer chains and crosslinking groups are nonsolvated which results in an effective pore size which is small and impervious to the hapten moiety or other reagents to thereby prevent the permeation and internalization thereof into the internal surface area of the gel particle. The particles further comprise a plurality of their respective chemically active functional groups at the external and internal surface areas thereof which are essential to the formation of a stable, covalent bond between the hapten moiety and the particle by a linking group, as will be described in greater detail hereinafter. It is to be appreciated that where a covalent bond is not formed between the hapten moiety and a functional group of the particle, such hapten moiety is likely to become nonspecifically bound the particle by nonspecific binding interactions, such as through ionic and hydrophobic binding interactions and the like. Such nonspecific binding of a hapten moiety to a particle results in a high degree of dissociation of such nonspecifically bound hapten moiety from the carrier material and subsequent leaching or slow release thereof when subjected to immunoassay test conditions or other aqueous environments.

Although a substantially stable, covalent bond can be formed between the hapten moiety and the functional groups as heretofore described in either an aqueous environment or an organic environment, the use of a nonswelling solvent is preferred according to the present invention in order to achieve the least amount of nonspecific binding of the hapten moiety to the gel particle, and, more particularly, substantially only to the external surface thereof according to the present invention. In particular, the hydrophilicity of the gel particle results in the undesirable swelling of the gel and increase in the permeation or internalization of the hapten moiety and other reagents into the gel particle when in an aqueous solution, whereas there is essentially no swelling or attendant increase in such permeation or internalization when in an organic solution or solvent containing little or no water. Accordingly, the use of a nonswelling solvent according to the present invention prevents the substantial swelling of the gel particle, which limits the covalent binding of the hapten moiety substantially only to the functional groups on the external surface of the gel particle by minimizing the permeation or internalization of the hapten moiety and other reagents into the particle. Such internalization would otherwise result in the undesirable formation of covalent bonds between the hapten moiety and functional groups which are present on the internal surface area of the gel particle as heretofore described. Such internalization of the hapten moiety and other reagents also results in the greater probability of the nonspecific adsorption of such internalized hapten moiety which would be difficult to remove with a wash solution and which could later leach out from the gel particle during the performance of an immunoassay and thereby result in decreased assay sensitivity and accuracy.

Accordingly, the immobilization of the hapten moiety to the gel particle is performed in a nonswelling organic solvent such as dimethylsulfoxide, dimethylformamide, acetone, chlorinated hydrocarbons, cyclic and acyclic alkylethers, and the like, preferably containing little or no water, which results in essentially no swelling of the gel particle and, accordingly, essentially no attendant increase in the permeation or internalization of the hapten moiety or other reagents into the particle. Since the negligible increase in particle size will result in a gel particle which is substantially impervious to and will effectively exclude the permeation of a hapten moiety and other reagents into the gel particle, any nonspecific binding of the hapten moiety is limited substantially only to the external surface of the gel particle. Any of the hapten moiety which becomes nonspecifically bound to the external surface of the gel particle is effectively removed with a nonswelling wash solution followed by an appropriately buffered rinse or wash solution, such as with an acidic salt solution. Upon the removal of such external, nonspecifically bound hapten moiety, the resulting immobilized hapten reagent comprises substantially all of the hapten moiety covalently bound to the external surface of the gel particle. The reagent thus is substantially stable in aqueous solutions as a result of the insignificant amount of the hapten moiety which is nonspecifically bound to the carrier material. In particular, it is to be appreciated that according to the present invention less than from about $1 \times 10^{-12}$ moles of the hapten moiety/gram of the resin, more usually less than from about $1 \times 10^{-13}$ moles of the hapten moiety/gram of the resin, preferably less than about $1 \times 10^{-14}$ moles of the hapten moiety/gram of the resin, will dissociate from the gel particle upon standing in an aqueous liquid for one week, such as a buffer solution, e.g., the phosphate-chloride assay buffer described in Example 5, to potentially result in an insignificant amount of leakage thereof during the performance of an immunoassay.

According to one preferred embodiment of the present invention, the carrier material of the immobilized hapten reagent is an aminoethyl-derivatized polyacrylamide resin, which is generally swellable in aqueous solutions and which can be prepared according to methods known in the art. According to such methods, a polyacrylamide resin is first prepared by the copolymerization of acrylamide and N,N'-methylenebisacrylamide [S. Hjerten and R. Mosbach, *Anal. Chem.*, Vol. 3, p. 109(1962)], to form, under suitable conditions, crosslinked polyacrylamide chains, followed by treatment with anhydrous ethylene-diamine [J. K. Inman and H. M. Dintzis, *Biochemistry, Vol.* 8, p 4074(1969)] to obtain an aminoethyl-derivatized polyacrylamide gel comprising a plurality of amine functional groups for use as the carrier material of the immobilized hapten reagent of the present invention. In addition to the derivatization of polyacrylamide with amine function groups by direct activation of the polyacrylamide resin and heretofore described, acrylamide and methylenebisacrylamide can be copolymerized with, for example, acrylic acid esters of N-hydroxysuccinimide or N-hydroxyphthalimide which can then be readily reacted with haptens containing primary amino functions, such as an aminohexyl group, which displace the active ester in the resin to provide the immobilized hapten reagent of the present invention [see, J. K. Inman, *Methods in Enzymology*, Vol. 34B, pp. 30–58(1974); G. L. Stahl et al., *J. Org. Chem.*, Vol. 44, p. 3424(1979); G. L. Stahl, et al., *J. Amer. Chem. Soc.*, Vol. 101, p. 5383(1979)].

The aminoethyl-derivatized polyacrylamide gel is particularly preferred because of its high capacity for the binding or immobilization of hapten thereto, as well as its low nonspecific adsorption properties. Further, the gel is also commercially available (Bio-Rad Laboratories, Richmond, CA, USA) having various aminoethyl capacities, generally from between about 1.0 and 2.0 meg. per dry gram of the resin. The gel also has a preferred pH range from about pH 2.0 to pH 10.0.

According to another embodiment of the present invention, the carrier material of the immobilized hapten reagent is a novel polyacrylamide sulfhydryl gel having, as the functional groups, a plurality of sulfhydryl groups, as described in greater detail in European Patent Application Publication No. 270,949. The polyacrylamide sulfhydryl gel is prepared from the free radical polymerization of acrylamide, bisacrylamide, and N,N'-bisacrylylcystamine and is particularly useful for the preparation of an immobilized glycopeptide reagent for use in the immunoassay determination of the glycosylated form of hemoglobin known as HbAlc. It is to be appreciated that the polyacrylamide sulfhydryl gel is similarly swellable in aqueous solutions. The swelling characteristics can be controlled by the ratio of monomers employed, the degree of crosslinking and the particular crosslinking group, and the active functional groups.

(b) Hapten Moiety

The hapten moiety of the immobilized hapten reagent can be the hapten under determination, or an analog thereof which is capable of binding to the specific binding partner thereof of the labeled reagent, and which hapten or binding analog thereof can be covalently linked to the external surface functional groups of a carrier material gel particle according to the present invention.

In particular, the hapten moiety of the immobilized hapten reagent of the present invention can be selected for the determination of any hapten for which a binding partner exists in a biological system or can be synthesized, and includes, but is not intended to be limited to, digoxin, digitoxigenin, digitoxin, digoxigenin, 12-0-acetyldigoxigenin, apolipoproteins such as apolipoprotein-Al and apolipoprotein-B100, and glycosylated peptide sequences such as the glucosylated N-terminal peptide sequence in the beta-subunit of human hemoglobin. Where an assay calls for the hapten moiety to be an analog of a glycoside analyte such as digoxin or digitoxin, it will be particularly preferred to select a hapten moiety which is free from glycosidic bonds, i.e., to select aglycones, for the formation of a stable, covalent bond between the hapten moiety and the gel particle as described above. Such aglycones include, but are not intended to be limited to, digoxigenin (the aglycone of digoxin), digitoxigenin (the aglycone of digitoxin), derivatives thereof, and the like. As will be understood by one skilled in the art, glycosidic bonds are relatively unstable and subject to hydrolysis under certain circumstances which could result in the dissociation of the hapten moiety as described above.

In addition, the hapten moiety can be selected from general classes of drugs, metabolites, hormones,, vitamins, toxins and the like -organic compounds. Haptenic hormones include thyroxine and triiodothyronine. Vitamins include vitamins A, B, e.g., $B_{12}$, C, D, E and K, fulic acid and thiamine. Drugs include antibiotics such as aminoglycosides, e.g., gentamicin, tobramycic, amikacin, sisomicin, kanamycin, and netilmicin, penicillin, tetracycline, terramycine, chloromycetin, and actinomycetin; nucleosides and nucleotides such as adenosine diphosphate (ADP) adenosine triphosphate (ATP), flavin mononucleotid (FMN), nicotinamide adenine dinucleotide [AND) and its phosphate derivative (NADP), thymidine, guanosine and adenosine; prostaglandins; steroids such as the estrogens, e.g., estriol and estradiol, sterogens, androgens, and adrenocortic]1 steroids; and others such as cyclosporin A, chenebarbital, phenytoin, primidone, ethosuximide, carbamazepine, valproate, theophylline, caffeine, proranolol, procainamide, quinidine, amitryptiline, cortisol, desipramine, disopyramide, doxepin, doxoubicin, nortryptiline, methotrexate, imipramine, lidocaine, procainamide, N-acetylprocainamide, amphetamines, catecholamines, and antihistamines. Toxins include acetyl T-2 toxin, alfatoxin, cholera toxin, citrinin, cytochalasins, staphylococcal enterotoxin B, HT-2 toxin, and the like.

(c) Linking Group

The linking group of the immobilized hapten reagent of the present invention can be selected from a number of linking groups known in the art to introduce a variety of functional groups which are capable of providing a stable, covalent linkage between a selected hapten moiety and the gel particle. For example, a gel particle can be covalently linked to a hapten moiety through linkages including, but not intended to be limited to, amide linkages, including acyl hydrazide; secondary amine linkages by alkylation of amino, hydrazide, and hydrazino groups; sulfide linkages by alkylation of thiols; and azo linkages through diazonium salts (see, J.K.

Inman, *Methods In Enzymology*, Vol. 34B, pages 30–58, 1974).

In particular, an amino-functionalized gel particle can be covalently linked to a hapten moiety by linking groups including, but not intended to be limited to, bifunctional residues of 1,6-hexamethylenediamine, 6-aminohexanol, 1,12-diamino-4,5-dioxadodecane, 1,17-diamino-3,6,9,12-15-pentaoxaheptadecane, bovine serum albumin, and 6-aminocaproic acid. The linking group can also be selected from a number of other linking groups known in the art, particularly in the case of the novel polyacrylamide sulfhydryl gel as heretofore described, and include, but are not intended to be limited to, bifunctional residues of bismaleimide (1,1'-[methylenedi-4,1-phenylene]bismaleimide), bismaleimido-hexane, and bismaleimido-hexaethylene glycol.

Similarly, hydroxylic polysaccharides can be activated with chemical reagents such as cyanogen bromide, dichloro-sym-triazines, trichlorotriazines, sodium meraperiodate, bisoxiranes or halohydrins, and the like. In such cases, the activated polysaccharide matrix is then reacted with nucleophilic groups such as amino, thiol, or hydroxyl present on the linking group to generate a stable immobilized hapten reagent according to the present invention. It is to be understood, of course, that a variety of other linking groups and methods for forming a stable, covalent bond between a gel particle and a hapten moiety according to the present invention can be employed and selected by one skilled in the art of affinity chromatography.

It is to be appreciated that important considerations in selecting an appropriate linking group to provide a stable, covalent bond between the hapten moiety and the gel particle according to the present invention are the correct spacial orientation and freedom from steric hindrance between the immobilized hapten reagent and the free species of a labeled reagent during the binding interaction therebetween. In particular, haptens which are closely bound to a solid support material are likely to interact very weakly with the specific binding partner of the labeled reagent because of the active site of a biological substance may be located deeply within the molecular structure thereof, and is therefor inaccessible to binding interactions. On the other hand, by binding such hapten to a solid support material through a flexible spacer arm or linking group of appropriate length, a substantial increase in binding is likely to occur. However, it has been demonstrated that substantially longer spacer arms will bind substances in a liquid test sample by hydrophobic binding interactions [P. O'Carra, et al., *Biochem. Soc. Trans.*, Vol. 1, pp.289–290 (1973)]. Thus, if the linking group is too short, the hapten may not bind to the specific binding partner therefor, and, if too long, non-specific binding effects become pronounced and reduce the selectivity of the separation of the bound species of a labeled reagent from the free species thereof.

Accordingly, the linking group can be selected by one skilled in the art apprised of the foregoing considerations so as not to substantially negate the novel features of the present invention. Selection of a stable linking group and linkage of the hapten moiety in a manner that essentially prevents internalization provides an immobilized hapten reagent according to the present invention which is substantially stable in aqueous solutions.

For example, the formation of a stable covalent bond between a hapten moiety and an aminoethyl-derivatized gel particle is achieved by forming an amide bond between the amine groups on the external surface of the gel particle and an N-hydroxysuccinimide-activated carboxy functionalized form of the hapten moiety in a nonswelling solvent liquid reaction environment, such as an organic solvent as heretofore described, preferably anhydrous. In particular, the hapten moiety is first activated with p-nitrophenyl chloroformate and then carboxyfunctionalized with 6-aminocaproic acid as the spacer are or linking group. The carboxy-functionalized hapten moiety is then activated with N-hydroxysuccinimide to form the ester thereof which is then reacted with the aminoethyl-derivatized gel particle in the anhydrous organic liquid reaction environment comprising dimethylformamide.

In particular, the ester of the activated hapten moiety is reacted with the gel in amounts from between about 50 $\mu$moles of the hapten moiety per dry gram of the resin to about 0.005 $\mu$moles of the hapten moiety per dry gram of the resin, preferably about 0.05 $\mu$moles of the hapten moiety per dry gram of the resin, wherein the concentration of the hapten moiety in the reaction mixture is between about 10 mM to about 1 $\mu$M, respectively, preferably about 10 $\mu$M. Any of the hapten moiety which is nonspecifically bound to the external surface of the gel particle will be removed with an organic wash solution as heretofore described, followed by an aqueous wash solution, wherein the hapten moieties covalently bound to the amine groups remain bound thereto, as well as during the subsequent performance of an immunoassay employing such immobilized hapten reagent.

In the case of the immobilized glycopeptide reagent of the present invention, the formation of a stable covalent bond between the glycosylated N-terminal peptide sequence in the beta-subunit of human hemoglobin (i.e., glycopeptide) and the novel polyacrylamide sulfhydryl gel is achieved by forming a sulfide bond between the sulfhydryl groups on the external surface of the gel particle and an activated form of the glycopeptide. In particular, the glycopeptide is first activated by a bismaleimide compound such as 1,1'-[methylene-4,1-phenylene]bismaleimide, bismaleimido-hexane, or bismaleimido -hexaethyleneglycol as the linking group. The activated glycopeptide is then reacted with the polyacrylamide sulfhydryl gel, previously reduced with, for example, dithiothreitol, in the nonswelling solvent to generate the sulfhydryl functional groups.

REAGENT SYSTEM

The present invention further provides a reagent system comprising all of the essential elements required to conduct a desired immunoassay method. The reagent system is presented in a commercially packaged form, as a composition or admixture where the compatibility of the reagents will allow, in a test device configuration, or more usually as a test kit, i.e., a packaged combination of one or more containers, devices or the like holding the necessary reagents, and usually including written instructions for the performance of immunoassays.

In particular, the reagent system will at least comprise (1) the immobilized hapten reagent of the present invention and (2) a labeled reagent, preferably a substantially pure monoconjugate preparation thereof as heretofore described, comprising a labeled form of a specific binding partner for the hapten, preferably a monovalent antibody fragment derived from a monoclonal antibody to the hapten under determination, labeled with an enzyme. Preferably, the reagent system will also include indicator means such as a test strip comprising a reagent pad incorporated with an indicator for the labeled reagent, preferably a chromogenic acridinone enzyme substrate as heretofore described where the label of the labeled reagent is an enzyme, which generates a detectable signal which can be measured and correlated to the amount of hapten present.

In particular, the present invention will now be illustrated, but is not intended to be limited, by the following examples:

EXAMPLE 1

Synthesis and Purification of Digitoxigenin

A solution of 765 mg (1 mmol) of digitoxin (Aldrich Chemical Co., Milwaukee, WI, USA; Lot No. JM02624ML) and 40 ml of a 1:1 (v/v) mixture of ethanol and 0.1 N HCl was stirred at 80° C. for 60 minutes and then cooled to room temperature. The solvent was evaporated under reduced pressure to a volume of approximately 10 ml of solvent which contained a solid, white precipitate, and the mixture was extracted with three 10 ml volumes of chloroform. The extracts were combined and washed with 10 ml of water, dried with magnesium sulfate, and the solvent evaporated under reduced pressure to obtain a white, solid material.

The white, solid material was dissolved in 4 ml of a 1:1 (v/v) mixture of chloroform and ethanol and then applied to a flash chromatography column (2.5 cm×60 cm) containing 40 g of silica gel (200–400 mesh) and eluted with a 1:1 (v/v) mixture of hexane and ethyl acetate. The fractions which eluted from the column were collected and analyzed by thin layer chromatography [9:1 v/v chloroform/methanol], and the fractions containing the digitoxigenin product were determined with a p-anisaldehyde spray reagent (900 ml 95% ethyl alcohol, 50 ml p-anisaldehyde, 50 ml concentrated sulfuric acid, and 50 ml acetic acid) by observing a blue coloration upon heating to indicate the presence of the desired digitoxigenin product. The product fractions were combined and the solvent was evaporated under reduced pressure to obtain a white, solid material which was then recrystallized from a 1:1 (v/v) mixture of ethanol and water to yield 300 mg of digitoxigenin in the form of shiny, white crystals.

EXAMPLE 2

Synthesis of 3-Digitoxigeninyl-p-nitrophenyl carbonate

Activated digitoxigenin was prepared by forming a reaction solution of 749 mg (2 mmol) of digitoxigenin (prepared according to Example 1) dissolved in 20 ml of anhydrous pyridine containing 61 mg (0.5 mmol) of 4-dimethylaminopyridine which was stirred with 524 mg (2.6 mmol) of p-nitrophenylchloroformate under argon at room temperature for 5 hours, and adding an additional 60 mg (0.3 mmol) of p-nitrophenyl chloroformate which was stirred under the same conditions for 15 hours. The solvent was evaporated under reduced pressure. The residue was suspended in 4 ml of chloroform and the suspension was applied to a flash chromatography column (3 cm×60 cm) containing 100 g silica gel (230–400 mesh) and eluted with a 1:1 (v/v) mixture of hexane and ethyl acetate. The fractions which eluted from the column were collected and analyzed by thin layer chromatography [9:1 (v/v) chloroform/methanol], and the fractions containing 3-digitoxigeninyl-p-nitrophenyl carbonate were determined with p-anisaldehyde spray reagent by observing a blue coloration upon heating to indicate the presence of the desired product. The product fractions were combined and the solvent was evaporated under reduced pressure to obtain a solid product which was then recrystallized from a mixture of hexane and chloroform to yield 279 mg of 3-digitoxigeninyl-p-nitrophenyl carbonate in the form of pale, yellow crystals.

EXAMPLE 3

Synthesis of 3-0-(5-carboxypentan-1-carbamoyl)digitoxigenin

Activated digitoxigenin was carboxy functionalized by forming a reaction solution of 1.08 g (2 mmol) of 3-digitoxigeninyl-p-nitrophenyl carbonate (prepared according to Example 2) dissolved in 50 ml of anhydrous pyridine which was stirred at room temperature while a solution of 315 mg (2.4 mmol) of 6-aminocaproic acid and 337 μl (2.4 mmol) of 6-aminocaproic acid and 337 μl (2.4 mmol) of triethylamine in 10 ml of a 1:1 (v/v) mixture of pyridine and water was slowly added during the course of a 5 minute time period. The reaction mixture was then stirred at room temperature for 21 hours and the solvents evaporated under reduced pressure. The residue was then dissolved in 25 ml of anhydrous toluene, and the solvent evaporated under reduced pressure.

The residue was dissolved in 5 ml of a 200:10:1 (v/v) mixture of methylene chloride, methanol and acetic acid and then applied to a flash chromatography column (5 cm×60 cm) containing 200 g of silica gel (230–400) mesh) and eluted with a 200:10:1 mixture of methylene chloride, methanol and acetic acid. The fractions which eluted from the column were collected and analyzed by thin layer chromatography [200:10:1 (v/v) methylene chloride, methanol and acetic acid] and the fractions containing 3-0-(5-carboxypentan-1-carbamoyl)digitoxigenin were determined with p-anisaldehyde spray reagent by observing a blue coloration upon heating to indicate the presence of the desired product. The product fractions were combined and the solvents were evaporated under reduced pressure to obtain a clear, oil product which was then crystallized with 10 ml of anhydrous ethyl ether to obtain a white, solid product which was collected by filtration and dried under high vacuum at 40° C. for 1 hour to yield 568 mg of 3-0-(5-carboxypentan-1-carbamoyl) digitoxigenin in the form of a white solid.

EXAMPLE 4

Activation of 3-0-(5-carboxypentan-1-carbamoyl)digitoxigenin with N-hydroxysuccinimide The ester of carboxy-functionalized digitoxigenin was prepared by forming a reaction MS-1455-CIP solution of 64 mg (117 μmol) of 3-0-(5-carboxypentan-1-carbamoyl)digitoxigenin (prepared according to Example 3) dissolved in 2 ml of anhydrous N,N-dimethylformamide (DMF) which was stirred under argon at room temperature and 28 μl [200 μmol) of triethylamine, 15 mg (130 umol) of N-hydroxysuccinimide and 27 mg (130 μmol) of N,N-dicyclohexylcarbodiimide were added. After 24 hours, the dicyclohexylurea which precipitated was removed by filtration and the filtrate containing the N-hydroxysuccinimide ester of 3-0-(5-carboxypentan-1-carbamoyl)digitoxigenin was diluted to 11.111 ml with DMF. Typically, this reaction does not proceed to completion.

EXAMPLE 5

Synthesis of N-hydroxysuccinimide Ester of 3-0-(5-carboxypentan-1-carbamoyl)digitoxigenin Covalently Bound to Aminoethyl BIO-GEL®P-2 Resin An immobilized hapten reagent of the present invention comprising digitoxigenin covalently bound to the external amine groups of an aminoethyl derivatized polyacrylamide gel particle was prepared by first forming a suspension of 2 grams of Aminoethyl BIO-GEL® P-2 resin (Bio-Rad Laboratories, Richmond, CA, USA; Lot No. 28945, 1.39 meq. amine functional groups/dry gram of resin) in 10 ml of DMF which was incubated at room temperature for 48 hours. A 10 ml aliquot of the supernate from the aminoethyl-derivatized BIO-GEL® P-2 resin in the DMF solution was removed and replaced with 10 ml of the activated digitoxigenin in DMF prepared according to Example 4 to form a reaction solution comprising 50 μmoles of activated digitoxigenin per dry gram of the resin and gently mixed on a rotary mixer (end-over-end agitation) at room temperature for 48 hours.

Similarly, the procedure described above was followed for preparing reaction solutions comprising 5 umoles, 0.5 μmoles, and 0.05 μmoles of activated digitoxigenin per dry gram of resin by removing 1.0 ml, 0.1 ml, and 0.01 ml of the supernate of similarly prepared BIO-GEL® P-2 resin in DMF, and replacing the removed volumes with 1.0 ml, 0.1 ml, and 0.01 ml of the activated digitoxigenin in DMF solution prepared according to Example 4, respectively.

The four samples of the immobilized hapten reagent of the present invention comprising digitoxigenin covalently linked to the oC aminoethyl-derivatized BIO-GEL® P-2 resin prepared as heretofore described were each collected by filtration and washed with ten 10 ml volumes of DMF and then with five 10 ml volumes of a buffered wash solution (hereinafter referred to as "wash buffer") comprising 2M NaCl and 0.1 M acetic acid (pH 2.3). The washed reagent samples were poured into columns and further washed with 14 bed volumes of the wash buffer. A 2-3 ml aliquot from each of the washed reagent solutions were poured into small columns and washed with 50 ml water followed by 50 ml of an assay buffer [pH 7.4] containing 0.05 M sodium phosphate, 0.05 M sodium chloride, 0.001 M magnesium chloride, 100 μg/ml bovine serum albumin, and 0.02% sodium azide (hereinafter referred to as assay buffer), and finally resuspended in a sufficient amount of the assay buffer to yield a suspension having a volume twice that of the volume of the settled resin (i.e., 50% crit). The remaining 7-8 ml of the washed resin samples were then washed with 60 ml of water and lyophylized from 50% crit.

EXAMPLE 6

Experimental Results

The immobilized digitoxigenin reagent resins prepared according to Example 5 were compared with digitoxigenin control resins similarly prepared with carboxy-functionalized digitoxigenin which was not activated with N-hydroxysuccinimide (NOS), in order to demonstrate the extent of covalent binding and non-specific binding in the immobilized digitoxigenin reagent when prepared according to the present invention. Such controls were employed because the formation of the NOS-ester of digitoxigenin does not proceed to 100% completion and, accordingly, nonactivated digitoxigenin is nevertheless present which could nonspecifically bind to the resin.

a Evaluation of Covalent Binding of Digitoxigenin to Resin.

The control resins were prepared by first removing 10.0 ml, 1.0 ml and 0.01 ml of supernate from the respective suspensions of 2 grams of aminoethyl derivatized BIO-GEL ® P-2 resin in 10 ml of DMF according to Example 5, and replacing the respective volumes thereof with solutions of nonactivated carboxy-functionalized digitoxigenin prepared according to Example 3. The same procedure as in Example 5 was then followed to prepare the respective control resins comprising digitoxigenin nonspecifically bound to aminoethyl derivatized BIO-GEL ® P-2 resin. The four immobilized digitoxigenin reagent resins prepared according to Example 5, and the four digitoxigenin control resins prepared according to the present example, were each evaluated in a heterogeneous immunoassay employing a 1.0 nM solution of monovalent antibody fragment (Fab) of a monoclonal antibody (see, for example, Porter, *Biochem. J.*, Volume 73, p. 119 [1959] and Nisonoff, *Methods Med. Res.*, Volume 10, p. 132 [1964]) to digoxin labeled with β-galactosidase (see, for example, Ishikawa, *J. Biochem.*, Volume 96, p. 659 [1984]; Kato et al., *J. Immunol,* Volume 116, p. 1554 [June 1976]; and Yoshitake et al., *Euro. J. Biochem.*, Volume 101, p. 395 [1977]) in the assay buffer solution (pH 7.4) of Example 5 as the labeled reagent, together with a normal human serum test sample (ASSAY I) and a normal human serum test sample containing 300 ng/ml digoxin (ASSAY II) as control samples, according to the following immunoassay protocols.

(i) ASSAY I (1) A first reaction mixture comprising 200 μl of the labeled reagent and 30 μl of the normal human serum sample was incubated for 5 minutes at room temperature;

(2) a second reaction mixture comprising 100 μl from the first reaction mixture from step (1) of the present assay and 100 μl of resin (obtained from the resin mixture with 50% of a settled resin volume, i.e., 50% crit) was rotated end-over-end (30 rpm) for 10 minutes at room temperature; and (3) the resin from step (2) of the present assay was permitted to settle for 1 minute, and a 30 μl aliquot of the supernatant was applied to a reagent pad incorporated with resorufin-μ-galactopyranoside (Hoffman et al., *Analytica Chimica Acta,* Volume 163, p. 67 [1984]) to determine the enzyme activity of the B-D-galactosidase of the labeled reagent.

(ii) ASSAY II (1) A first reaction mixture comprising 200 μl of the labeled reagent and 30 μl of the normal human serum sample containing 300 ng of digoxin/ml thereof was incubated for 5 minutes at room temperature;

(2) a second reaction mixture comprising 100 μl from the first reaction mixture of step (1) of the present assay and 100 μl of resin (50% crit) was rotated end-over-end (30 rpm) for 10 minutes at room temperature; and (3) the resin from step (2) of the present assay was permitted to settle for 1 minute, and a 30 μl aliquot of the supernatant was applied to a reagent pad incorporated with resorufin-β-D-galactopyranoside.

The rate of color formation resulting from the interaction between the β-D-galactosidase and the resorufin-β-D-galactopyranoside was measured at 560 nM between about 60 to 80 seconds after the sample application to the reagent pad, in order to determine the β-D-galactosidase activity of the labeled reagent from the supernatant, i.e., the bound species. The reactivity measurements (Table 1) were made on a Seralyzer ® reflectance photometer (Miles Inc., Elkhart, IN USA) attached to an HP-85 computer (Hewlett-Packard Company, Palo Alto, CA, USA) through a multiple port interface, wherein the extent of binding of conjugate to the resin particle was determined by calculating the amount of background signal (% background) according to the following equation:

$$\% \text{ BACKGROUND} = \frac{\text{REACTIVITY OF ASSAY I}}{\text{REACTIVITY OF ASSAY II}} \times 100,$$

the results of which are summarized in Table 1. It is to be understood that a low value for the % background indicates good binding of the conjugate by the resin which can only take place in the absence of leachable, nonspecifically adsorbed hapten.

TABLE 1

| Digitoxigenin Concentration (μMoles/dry gram) | Reagent Pad Reactivity × 10³ | | % Background |
|---|---|---|---|
| | ASSAY I | ASSAY II | |
| Invention Resins | | | |
| 50.0 | 1.32 | 10.3 | 12.7 |
| 5.0 | 1.91 | 10.9 | 17.5 |
| 0.5 | 0.99 | 10.5 | 9.4 |
| 0.05 | 1.17 | 10.2 | 11.4 |
| Control Resins | | | |
| 50.0 | 4.98 | 10.3 | 48.3 |
| 5.0 | 8.01 | 10.5 | 76.4 |
| 0.5 | 10.1 | 11.2 | 89.4 |
| 0.05 | 11.1 | 11.5 | 96.4 |

Similarly, the lyophilized resin was tested according to the following assay procedures:

(i) ASSAY III (1) A first reaction mixture comprising 375 μl of the labeled reagent and 30 ul of the normal human serum sample was incubated 10 minutes at room temperature;

(2) a second reaction mixture comprising 200 μl from the first reaction mixture from step (1) of the present assay and 10 mg of lyophilized resin was vortexed for 5 minutes at room temperature; and (3) the resin from step (2) of the present assay was permitted to settle for 1 minute, and a 30 μl aliquot of the supernatant was applied to a reagent pad incorporated with resorufin-β-Dgalactopyranoside (Hoffman et al., Analytica Chimca Acta, Volume 163, p. 67 [1984]) to determine the enzyme activity of the β-D-galactosidase of the labeled reagent.

(ii) ASSAY IV (1) A first reaction mixture comprising 375 μl of the labeled reagent and 30 μl of the normal human serum sample containing 300 ng of digoxin/ml was incubated for 10 minutes at room temperature;

(2) a second reaction mixture comprising 200 μl from the first reaction mixture of step [1] of the present assay and 10 mg of lyophilized resin was vortexed for 5 minutes at room temperature; and (3) the resin from step (2) of the present assay was permitted to settle for 1 minute, and a 30 μl aliquot of the supernatant was applied to a reagent pad incorporated with resorufin-β-D-galactopyranoside.

The rate of color formation resulting from the interaction between the β-D-galactosidase and the resorufin-β-D-galactosidase was measured as heretofore described. The amount of binding of conjugate to the resin particle was determined by calculating the amount of background signal (% background) according to the following equation:

$$\% \text{ BACKGROUND} = \frac{\text{REACTIVITY OF ASSAY III}}{\text{REACTIVITY OF ASSAY IV}} \times 100.$$

the results of which are summarized in Table 2.

TABLE 2

TESTING OF THE DIGOXIN ASSAY BACKGROUNDS WITH LYOPHILIZED AMINOETHYL-DERIVATIZED BIOGEL ® P-2:DIGITOXIGENIN

| Digitoxigen Level μMole/dry Gram | Reactivity × 10³ | | % Background |
|---|---|---|---|
| | ASSAY III | ASSAY IV | |
| Invention Resins | | | |
| 50 | 4.49 | 11.9 | 37.9 |
| 5 | 6.40 | 12.5 | 51.1 |
| 0.5 | 2.13 | 12.6 | 17.0 |
| 0.05 | 2.14 | 12.4 | 17.2 |
| Control Resins | | | |
| 50 | 8.86 | 12.7 | 69.6 |
| 5 | 12.1 | 12.9 | 94.0 |
| 0.5 | 12.4 | 12.7 | 97.8 |
| 0.05 | 13.0 | 12.7 | 102.4 |

The significant difference in the background signal between the immobilized digitoxigenin reagent resin of the present invention and the control resin indicates that the digitoxigenin moiety was strongly bound to the resin by a stable, covalent bond. The ability of the control resins which are treated with the free carboxylic acid form of the hapten to bind some of the conjugate indicates that there is a strong nonspecific absorption of the compound to the resin. As the concentration of the free acid form is decreased, such nonspecific absorption also decreases. It is at such low hapten concentrations that the immobilized hapten reagent resin of the present invention can be obtained which performs optimumly in its lyophilized form (Table 2).

b. Evaluation of Stability of Immobilized Digitoxigenin Reagent

The leaching of digitoxigenin from the immobilized digitoxigenin reagent prepared according to the present invention was evaluated according to the following assay, employing test samples of 170 μl assay buffer (low reactivity control), 150 nM digoxin in assay buffer (high reactivity control), or 170 μl of the supernatants from the 50 μmol/dry gram resin, 5 μmol/dry gram resin, 0.5 μmol/dry gram resin, and 0.05 μmol/dry gram resin which were stored in the assay buffer for 1 week at 4° C (after storage, the resins were first resuspended and permitted to settle before the supernatant was removed):

(i) A first reaction mixture comprising 30 μl of normal human serum and 30 μl of a 6.7 nM solution of the conjugate was mixed with one of the aforementioned test samples and incubated for 5 minutes at room temperature;

(ii) a second reaction mixture comprising 100 μl of the first reaction mixture and 100 μl of a 50% crit of a freshly washed Sephadex ® G10-BSA-ouabain resin as heretofore described (obtained from duPont Digoxin Assay Reagent Kit, Catalog No. 705797901, E.I. duPont de Nemours and Company, Inc., Wilmington, DE, USA) was rotated end-over-end (30 rpm) for 20 minutes at room temperature; and (iii) the resin from step (ii) was permitted to settle for 1 minute, and a 30 μl aliquot of the supernatant was applied to a reagent pad incorporated with resorufin-B-D-galactopyranoside and the rate of color formation measured on a Seralyzer ® reflectance photometer as heretofore described. The amount of interference to conjugate binding by digitoxigenin which leached into the assay medium was determined by the following calculations:

$$\% \text{ BACKGROUND} = \frac{\text{REACTIVITY OF SAMPLE}}{\text{REACTIVITY OF HIGH REACTIVITY CONTROL}} \times 100.$$

wherein

% INCREASE IN BACKGROUND =

% BACKGROUND OF SAMPLE −

% BACKGROUND OF LOW REACTIVITY CONTROL, the results of which are summarized in Table 3.

TABLE 3

| Sample | Reactivity | % Background | Increase in % Background |
|---|---|---|---|
| High reactivity control | 0.0116 | NA | NA |
| Low reactivity control | 0.0018 | 15.6 | NA |
| Supernatant of 50 μmol/g | 0.0054 | 46.8 | 31.2 |
| Supernatant of 5 μmol/g | 0.0058 | 50.1 | 34.5 |
| Supernatant of 0.5 μmol/g | 0.0026 | 22.3 | 6.7 |
| Supernatant of 0.05 μmol/g | 0.0020 | 17.7 | 2.1 |

The results indicate that leaching of digitoxigenin, i.e., nonspecifically adsorbed, from the resins prepared at concentrations of 0.5 and 0.05 μmoles digitoxigenin/gram of resin, particularly at 0.05 μmoles digitoxigenin/gram of resin, was minimized. The minimal amount of leaching, particularly at 0.5 μmol/g and 0.05 μmol/g as shown by the data above, clearly demonstrates that the resins prepared according to the present invention, i.e., in an anhydrous organic solvent with a reaction mixture dilution as heretofore described, posses a substantially stable covalent bond between the digitoxigenin and the resin, and exhibit a minimal amount of loosely or nonspecifically bound digitoxigenin wherein the amount of digitoxigenin which is leached substantially decreases at such higher dilutions.

c. Dose Response to Digoxin

The 0.05 μmoles digitoxigenin/gram resin prepared according to the present invention was washed with a buffer solution (2 M NaCl and 0.1 M acetic acid, pH 2.3), followed by water, and then dried by lyophylization. The lyophylized resin was then employed in an immunoassay for the determination of digoxin from a liquid test sample, employing, as the labeled reagent, a substantially pure monoconjugate preparation comprising a single monovalent antibody fragment (Fab') derived from a monoclonal antibody against digoxin covalently linked to a single β-D-galactosidase component. The monoconjugate was obtained from a conjugate reaction mixture comprising a monovalent and multivalent conjugates, free β-D-galactosidase components and free Fab' components, which was electrophoretically purified on an electrophoretic polyacrylamide gel as described in European Patent Application Publication No. 270,930. The immunoassay also employed, as the chromogenic enzyme substrate, an acridinone-β-D-galactopyranoside comprising a 7-hydroxy-9,9-dimethyl-9H-acridin-2-one derivatized at the 7-position thereof with a β-D-galactose residue as described in European Patent Application Publication No. 270,946, as follows:

(i) A reaction mixture comprising 875 μl of a 0.30 nM solution of the monoconjugate labeled reagent and 35 μl of a serum test-sample containing digoxin was incubated at room temperature for 6 minutes;

(ii) a reaction mixture comprising 780 μl of the reaction mixture of step (i) and 30 mg of lyophilized 0.05 μmoles digitoxigenin/gram resin was agitated for 4 minutes, and the resin was separated from the solution by a porous plastic filter; and (iii) a 30 μl aliquot was removed from the filtrate of the reaction mixture of step (ii) and applied to a reagent strip incorporated with acridinone-8-D-galactopyranoside.

The rate of color formation resulting from the interaction between the β-D-galactosidase and the acridinone-β-D-galactopyranoside was measured at 630 nm between about 60 to 80 seconds after sample application to the reagent pad, in order to determine the β-D-galactosidase activity of the monoconjugate labeled reagent from the filtrate, i.e., the bound species (Table 4). The resulting dose response to digoxin based upon the data shown in Table 4 is shown in FIG. 1.

TABLE 4

| Dose Response to Digoxin | |
|---|---|
| Digoxin concentration ng/ml | Reactivity × $10^3$ |
| 0 | 1.01 |
| 0.6 | 1.71 |
| 1.2 | 2.31 |
| 2.4 | 3.59 |
| 3.6 | 4.79 |
| 5.0 | 6.28 |

EXAMPLE 7

Synthesis of Crosslinked Polyacrylamide-Sulfhydryl Copolymer Gel Particles

Under argon, acrylamide (40%), bisacrylamide (10%) and N,N'bisacrylylcystamine (3.4%) were mixed with 30 ml of water. The temperature of the mixture was increased to 45°–50° C. in order to dissolve all of the solids. After 100 μl N,N,N',N'-tetramethylethylenediamine was added, the mixture was cooled to 40° C., and 25 mg ammonium persulfate was added and the solution was allowed to polymerize into the form of a bulk polymer in an ice bath. After 3 hours, the bulk polymer was removed from the vessel as a transparent, solid material and mixed with water and homogenized with a mechanical blender to obtain a gel suspension. The gel suspension was first sieved on an 85 mesh screen (USC designation) to obtain gel particles having diameters less than 150 μm in diameter, which were then sieved on a 400 mesh screen to obtain particles from between 38 μm and 150 μm in diameter. The resulting 38 um-150 um particles were washed well with water, and the gel filtered and washed with ethanol and finally dried by suction and vaccum.

EXAMPLE 8

Synthesis of Immobilized Glyopeptide Reagent

An immobilized hapten reagent comprising a glycopeptide covalently bound to the external sulfhydryl functional groups of the polyacrylamide gel prepared according to Example 7 was prepared as follows:

(a) The crosslinked polyacrylamide sulfhydryl copolymer gel prepared according to Example 7 (2.0 g) was first washed (4×5 ml) with dimethylformamide (DMF), drained and mixed with 400 mg dithiothreitol (DTT) and 0.5 ml DMF. The mixture was stirred and vortexed occasionally at room temperature. After 1 hour, the liquid was drained and the gel was kept under argon and washed with argon-purged DMF until no DTT was detected from the wash.

(b) In a separate vessel, a 800 μl solution of a glycopeptide (the glucosylated N-terminal peptide sequence in the beta-subunit of hemoglobin as described in European Patent Application Publication No. 185,870) at a concentration of 1.0 mg/100 μl water was mixed with a solution of 200 μl of bismaleimido-hexaethylene glycol (1.0 mg in 100 μl DMF) and 600 μl DMF. After 10 minutes at room temperature, the solution was added to the activated gel from step (a) of the present example. The gel mixture was stirred and vortexed occasionally for 2 hours. The gel was drained and washed with DMF (8×2ml), a solution of 2M NaCl and 0.1 N acetic acid (6×5ml), water (150ml) and ethanol (4×10ml). The gel was then dried by suction and under vacuum to give 2.0 g of the immobilized glycopeptide reagent of the present invention comprising the glycopeptide covalently bound substantially only to the external sulfhydryl functional groups of the crosslinked copolymer gel particle.

EXAMPLE 9

Immobilized Glycopeptide Reagent Reactivity Assay

The immobilized glycopeptide reagent (resin) prepared according to Example 8 was evaluated to determine the level of unbound label (background) employing, as a labeled reagent, a monoconjugate preparation of a monovalent antibody fragment (Fab') labeled with β-D-galactosidase. The monovalent antibody fragment was derived from a monoclonal antibody specific for the glucosylated N-terminal peptide sequence (8 amino acids) in the beta-subunit of human hemoglobin (see European Patent Application Publication No. 185,870) according to the methods described by Porter and Nisonoff, supra, and labeled with β-D-galactosidase according to the methods described by Ishikawa, Kata et al., and Yoshitake et al., supra. The monovalent antibody fragment 8-D-galactosidase conjugate was electrophoretically purified on a polyacrylamide gel to result in a substantially pure monoconjugate preparation comprising a single Fab' component and a single β-D-galactosidase component, as described in European Patent Application Publication No. 270,930 referenced to above.

(a) To a solution of 250 μl of the monoconjugate labeled reagent, 30 μl of buffer (pH 7.4, 0.05M sodium phosphate, 0.05M sodium chloride, 1 mM magnesium chloride, 100 mg/ml bovine serum albumin, and 0.02% sodium azide) was added;

(b) 270 μl aliquot of the solution from step (a) of the present example was mixed with 10-20 mg of the immobilized glycopeptide reagent (resin) and the suspension was rotated end-over-end for 30 minutes at room temperature; and (c) the resin was removed by filtration and a 30 μl aliquot of the filtrate was applied to a reagent pad incorporated with resorufin-β-D-galactopyranoside.

The reactivity measurements were made with a Seralyzer ® reflectance photometer as heretofore described and the ratio of the reactivities measured in this manner to the reactivity of the labeled reagent without the treatment of the resin were reported as % background (see Table 5).

TABLE 5

| Immobilized Glycopeptide Reagent Sample # | Bismaleimido | Glycopeptide concentration | Reactivity | % Background |
|---|---|---|---|---|
| I | PEG-6 | 1 mg/g | 0.01802 | 48 |
| II | PEG-6 | 1 mg/g | 0.01992 | 62 |
| III | PEG-6 | 1 mg/g | 0.01655 | 59–64 |
| IV | PEG-6 | 2 mg/g | 0.02349 | 52.7 |
| V | PEG-6 | 4 mg/g | 0.01909 | 29.1 |
| VI | PEG-6 | 6 mg/g | 0.05032 | 76.7 |
| VII | methylene-diphenylene | 2 mg/g | 0.04202 | 89 |
| VIII* | PEG-6 | 2 mg/g | 0.06560 | 100 |
| IX** | PEG-6 | 1 mg/g | 0.05713 | 121 |

*Sequential addition of bismaleimido and glycopeptide
**Not activated by DTT

EXAMPLE 10

Immunoassay for the Determination of HbAlc (a) Varying concentrations (30 μl) of denatured blood, i.e., HbAlc (FIG. 2), were added to 250 μl solutions of the labeled reagent [Example 9) and the mixtures allowed to stand for 10 minutes at room temperature;

(b) a 270 μl aliquot from each mixture was mixed with 15 mg of the immobilized glycopeptide reagent (Example 8) and rotated end-over-end for 10 minutes at room temperature; and (c) the resin was removed by filtration and 30 μl of the filtrate was applied to a reagent pad incorporated with resorufin-β-D-galactopyranoside.

Figure 2:
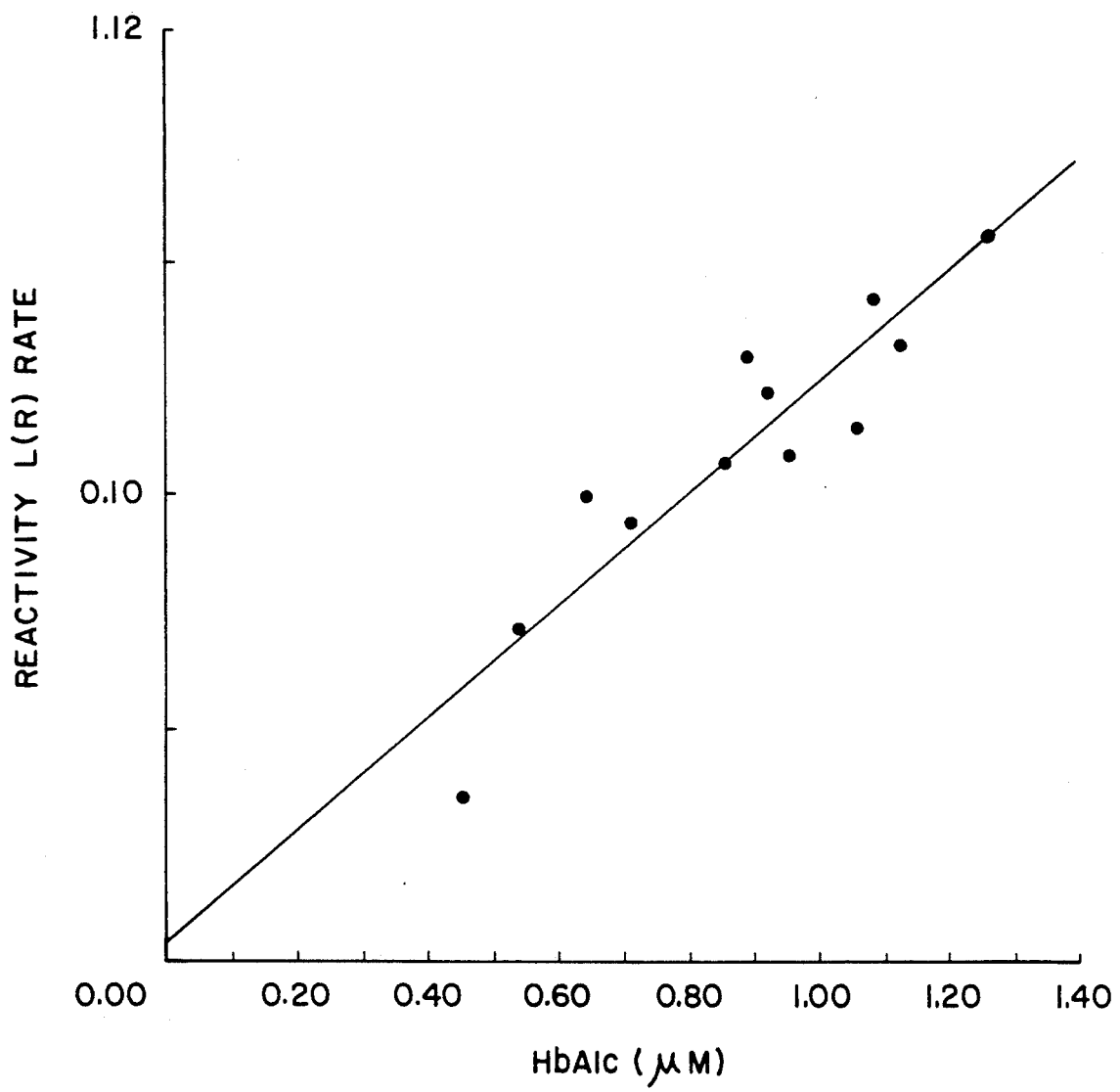
FIG. 2 is a graph which illustrates the reactivity of an immobolized glycopeptide reagent of the present invention in an immunoassay for the determination of the amount of glycosylated hemoglobin HbAlc in a whole blood sample.

The reactivity measurements were made with a Seralyzer ® reflectance photometer as heretofore described and the reactivities were found to be directly proportional to the concentrations of HbAlc present in whole blood (see FIG. 2).

EXAMPLE 11

Isolation of the N-hydroxysuccinimide Ester of 3-0-(5-carboxypentan-1-carbamoyl)digitoxigenin The ester of carboxy-functionalized digitoxigenin was prepared by forming a reaction solution of 6.384 g (12 mmol) of 3-0-(5-carboxypentan-1-carbamoyl)-digitoxigenin (prepared according to Example 3) dissolved in 90 mL of anhydrous N,N-dimethylformamide (DMF) which was stirred under argon at room temperature and 5.52 mL (39.6 mmol) of triethylamine, 4.56 g (39.6 mmol) of N-hydroxysuccinimide and 7.956 g (39.6 mmol) of N,N-dicyclohexylcarbodiimide were added. After 20 hours, the dicyclohexylurea which precipitated was removed by filtration and the filtrate was evaporated under high vacuum at 35° C. to obtain a clear oil. The oil was dissolved in chloroform and chromatographed using a Waters Prep LC/System 500A Liquid Chromatograph (Waters Associates; Milford, MA, USA) equipped with four Prep PAK®-500/SILICA cartridges. Separation was obtained using ethyl acetate as the eluent. Fractions which contained the pure ester product were combined and the solvent was removed under vacuum at 30° C. leaving a clear, colorless oil. The oil was redissolved in a small volume of ethyl acetate and allowed to stand at 5° C. The white crystalline solid which formed was collected by filtration to give 3.85 g of the N-hydroxysuccinimide ester of 3-0-(5-carboxypentan-1-carbamoyl)digitoxigenin.

EXAMPLE 12

Synthesis of N-hydroxysuccinimide Ester of 3-0-(5-carboxypentan-1-carbamoyl)digitoxigenin Covalently Bound to Aminoethyl Bio-Gel® P-2 Resin An immobilized hapten reagent of the present invention comprising digitoxigenin covalently bound to the external amine groups of an aminoethyl-derivatized polyacrylamide gel particle was prepared using the following procedure. One hundred grams (100 g) of Aminoethyl Bio-Gel®P-2 resin (Bio-Rad Laboratories, Richmond, CA, USA; Lot No. 34358, 1.09 meq. amine functional groups/dry gram of resin) was placed inside a 5.0 L Reaction Flask for Solid-Phase Peptide Synthesis (Aldrich Chemical Company, Inc., Milwaukee, WI, USA; Catalog No. Z16,230-2) equipped with an air-driven glass stir rod and teflon paddle. The stopcock was closed and 400 mL of anhydrous dimethylformamide (DMF) was added. The mixture was stirred for five minutes and then allowed to stand at room temperature for fifteen hours with the reaction flask stoppered. The DMF was suction-drained from the reaction flask and fresh DMF (400 mL) was added. The resin was resuspended by stirring for five minutes after which the DMF was again drained off. This wash procedure was repeated four more times. DMF (500 mL) was added and the mixture was stirred as a solution of 3.0 mg (0.05 umol) of the N-hydroxysuccinimide ester of 3-0-(5-carboxypentan-1-carbamoyl)digitoxigenin (prepared according to Example 11) in 20 mL of DMF was added dropwise over five minutes. After two hours the reaction flask was drained and the resin was washed by stirring for ten minutes with DMF (1.0 L). The wash procedure was repeated four more times with fresh DMF (1.0 L per wash). The resin was then washed five times with 0.1 M sodium borate, pH 9.3, using 400 mL for each wash and stirring ten minutes between washes. The resin was stirred with 500 mL of 0.1M sodium borate, pH 9.3, and 100 mL (1 mole) of acetic anhydride was rapidly added. After stirring for one hour the reaction flask was suction drained and the resin was washed ten times with $H_2O$ (1 L per wash) stirring for ten minutes between washes. The resin was collected by filtration and placed at $-60°$ C. for fifteen hours after which it was allowed to thaw at 25° C. for three hours before a final wash with $H_2O$ consisting of five washes (1.0 L each) at five minute intervals. The resin was then dried by lyophilization to give the immobilized hapten reagent of the present invention as a free flowing white powder.

What is claimed is:

1. A method of preparing a stable immobilized hapten reagent for use in the specific binding assay determination of a hapten or binding analog thereof in a liquid test sample, the method comprising the steps of:
    (a) reacting a hapten moiety with a gel particle comprising a plurality of external and internal chemically active functional groups wherein the reaction is performed in a solvent in which the gel particle is substantially nonswollen and under conditions to form a covalent bond between the hapten moiety and said external active functional groups which is substantially stable in aqueous solutions;
    (b) washing the gel particle resulting from step(a) with a nonswelling solvent;
    (c) washing the gel particle resulting from step(b) with an aqueous solution; and
    (d) isolating the immobilized hapten reagent resulting from step(c) comprising said gel particle and said hapten moieties bound thereto wherein substantially all of said bound hapten moieties are covalently linked to the external surface functional groups by a linking group which is substantially stable in aqueous solutions.

2. The method of claim 1 wherein said gel particle is selected from the group consisting of polymers and copolymers of acrylic acid, agarose, cellulose, dextran, and their derivatives or mixtures thereof.

3. The method of claim 1 wherein the nonswelling solvent is an organic solvent.

4. The method of claim 3 wherein said organic solvent is selected from the group consisting of dimethylformamide, dimethylsulfoxide, acetone, chlorinated hydrocarbons, and cyclic and acyclic alkylethers.

5. The method of claim 1 wherein the hapten moiety is selected from the group consisting of drugs, metabolites, hormones, vitamins, and toxins.

6. The method of claim 1 wherein the hapten moiety is selected from the group consisting of digoxin, digitoxigenin, digitoxin, digoxigenin, and 12-0-acetyldigoxigenin.

7. The method of claim 1 wherein the hapten moiety is a glycosylated peptide sequence.

8. The method of claim 1 wherein less than from about $1 \times 10^{-12}$ moles hapten/gram gel particle dissociates from the gel particle of the immobilized hapten reagent upon standing in an aqueous solution for one week.

9. The method of claim 8 wherein less than from about $1 \times 10^{-13}$ moles hapten/gram gel particle dissociates from the gel particle of the immobilized hapten reagent upon standing in an aqueous solution for one week.

10. The method of claim 1 wherein the gel particle in its nonswollen state is substantially impervious to the hapten moiety.

11. The method of claim 1 wherein the gel particle is less than about 1,000 microns in diameter.

12. The method of claim 1 wherein the gel particle is from,-between, about 0.001 microns and about 850 microns in diameter.

13. The method of claim 1 wherein the gel particle is from between about 37 microns and about 75 microns in diameter. MS-1455-CIP 14. A substantially stable immobilized hapten reagent for use in the specific binding assay determination of a hapten or binding analog thereof in a liquid test sample, the immobilized hapten reagent comprising a gel particle which is substantially swellable in water and a plurality of hapten moieties bound thereto, said gel particle comprising a plurality of external and internal functional groups wherein substantially all of said bound hapten moieties are covalently linked to said external functional groups by a linking group which is substantially stable in aqueous solutions.

15. The immobilized hapten reagent of claim 14 wherein said gel particle is selected from the group consisting of polymers and copolymers of acrylic acid, agarose, cellulose, dextran, and their derivatives or mixtures thereof.

16. The immobilized hapten reagent of claim 14 wherein the hapten moiety is selected from the group consisting of drugs, metabolites, hormones, vitamins, and toxins.

17. The immobilized hapten reagent of claim 14 wherein the hapten moiety is selected from the group consisting of digoxin, digitoxigenin, digitoxin, digoxigenin, and 12-0-acetyldigoxigenin.

18. The immobilized hapten reagent of claim 14 wherein the hapten moiety is a glycosylated peptide sequence.

19. The immobilized hapten reagent of claim 14 wherein less than from about $1 \times 10^{-12}$ moles hapten/gram gel particle dissociates from the gel particle of the immobilized hapten reagent upon standing in an aqueous solution for one week.

20. The immobilized hapten reagent of claim 19 wherein less than from about $1 \times 10^{-13}$ moles hapten/gram gel particle dissociates from the gel particle of the immobilized hapten reagent upon standing in an aqueous solution for one week.

21. The method of claim 14 wherein the gel particle is less than about 1,000 microns in diameter.

22. The method of claim 14 wherein the gel particle is from between about 0.001 microns and about 850 microns in diameter.

23. The method of claim 14 wherein the gel particle, is from between about 37 microns and about 75 microns in diameter.

24. In an immunometric assay method for determining a hapten or analog thereof in a liquid test sample, wherein the test sample is contacted with a labeled antibody reagent capable of binding with said hapten or analog thereof and with an immobilized form of the hapten capable of binding with said antibody reagent, and wherein the amount of labeled antibody reagent which becomes bound to said hapten or analog thereof in the sample compared to that which becomes bound to the immobilized reagent is determined and related to the presence of the hapten or analog thereof in the test sample, the improvement which comprises employing as the immobilized reagent a substantially stable immobilized hapten reagent comprising a gel particle which is substantially swellable in water and a plurality of hapten moieties bound thereto, said gel particle comprising a plurality of external and internal functional groups wherein substantially all of said bound hapten moieties are covalently linked to said external functional groups by a linking group which is substantially stable in aqueous solutions.

25. The method of claim 24 wherein said gel particle is selected from the group consisting of polymers and copolymers of acrylic acid, agarose, cellulose, dextran, and their derivatives or mixtures thereof.

26. The method of claim 24 wherein the hapten moiety is selected from the group consisting of drugs, metabolites, hormones, vitamins and toxins.

27. The assay method of claim 24 wherein the hapten moiety is selected from the group consisting of digoxin, digitoxigenin, digitoxin, digoxigenin, and 12-0-acetyldigoxigenin.

28. The assay method of claim 24 wherein the hapten moiety is a glycosylated peptide sequence.

29. The assay method of claim 24 wherein less than from about $1 \times 10^{-12}$ moles hapten/gram gel particle dissociates from the gel particle of the immobilized hapten reagent upon standing in an aqueous solution for one week.

30. The assay method of claim 29 wherein less than from about $1 \times 10^{-13}$ moles hapten/gram gel particle dissociates from the gel particle of the immobilized hapten reagent upon standing in an aqueous solution for one week.

31. The method of claim 24 wherein the gel particle is less than about 1,000 microns in diameter.

32. The method of claim 24 wherein the gel particle is from between about 0.001 microns and about 850 microns in diameter.

33. The method of claim 24 wherein the gel particle is from between about 37 microns and about 75 microns in diameter.

* * * * *